United States Patent [19]

Langer

[11] Patent Number: 5,017,500
[45] Date of Patent: May 21, 1991

[54] FAT EXTRACTION PROCESS AND APPARATUS

[75] Inventor: Alfred Langer, Bornheim-Hersel, Fed. Rep. of Germany

[73] Assignee: C. Gerhardt Fabrik & Lager Chemischer Apparate GmbH & Co K.G., Bonn, Fed. Rep. of Germany

[21] Appl. No.: 255,745

[22] Filed: Oct. 11, 1988

[51] Int. Cl.$^5$ .............. G01N 1/00; B01D 11/02; C11B 1/10

[52] U.S. Cl. .................. 436/178; 422/99; 422/101; 422/280; 260/412.8; 203/DIG. 2

[58] Field of Search ............ 436/178, 43, 50, 60, 436/63; 422/62, 99, 101, 280; 202/161, 168, 169; 203/DIG. 2; 260/412.4, 412.8; 210/773

[56] References Cited

U.S. PATENT DOCUMENTS 3,798,133  3/1974  Randall .................. 422/280

FOREIGN PATENT DOCUMENTS 2949692  6/1981  Fed. Rep. of Germany ...... 422/101

Primary Examiner—Robert A. Wax
Assistant Examiner—William H. Beisner

[57] ABSTRACT

A process and apparatus for solvent extraction of fat from a sample. The sample is held in a thimble located in a sample vessel. The sample vessel holds solvent in which the sample is initially immersed. The solvent is vaporized by a heating unit and condenses on a cooling coil above the sample vessel. The condensed solvent is caught in a funnel equipped with a drain line leading to an external solvent collection vessel. A timer controlled valve opens and closes the drain line. The fat extraction process includes a boiling phase during which the valve is closed so that the condensed solvent overflows the funnel and returns to the sample vessel, a solvent level lowering phase during which the valve is open to direct solvent to the collection vessel until the solvent level in the sample vessel is below the sample, a washing phase during which the valve is closed to cause the condensed solvent to overflow the funnel and drip onto the sample, and a solvent recovery phase during which the valve is pen to direct the solvent to the collection vessel.

20 Claims, 1 Drawing Sheet

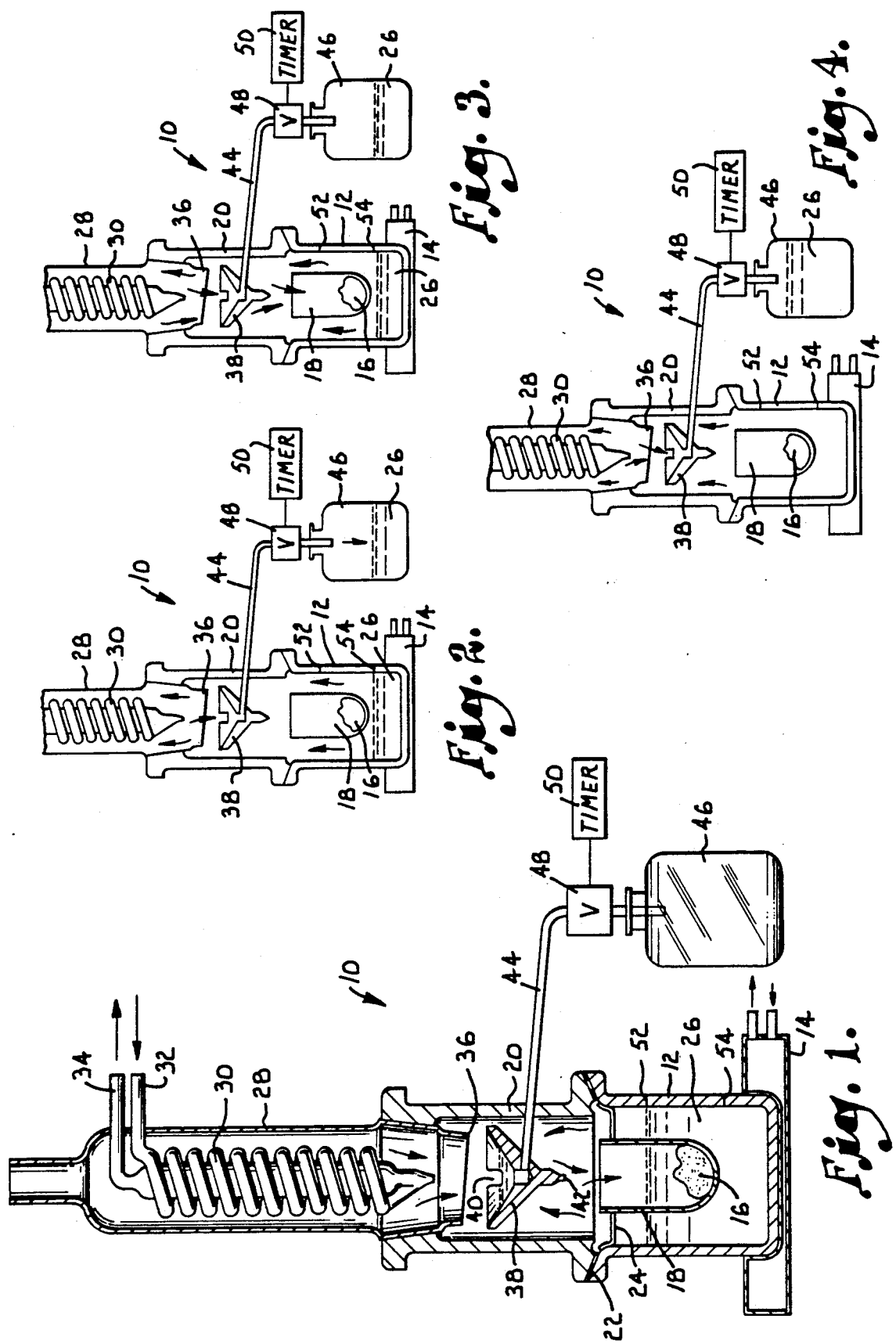

FAT EXTRACTION PROCESS AND APPARATUS

BACKGROUND AND SUMMARY OF THE INVENTION

This invention relates generally to solvent extraction and more particularly to a fat extraction process and apparatus which are well suited for automated operation.

Solvent extraction of fats and other substances has conventionally been carried out by a process known as the Soxhlet process. In the Soxhlet process, solvent is heated in a flask to vaporization, and the rising vapors are condensed on a cooling coil. The condensate drips onto a sample which is held below the cooling coil in a thimble. When the solvent level in the thimble rises above the sample, the solvent is siphoned off through a siphon tube and returned to the flask. The process is repeated continuously.

The main disadvantage of the Soxhlet process is the relatively long time that is required to complete the extraction. In addition, insertion and removal of the sample requires removal of the cooling coil along with its inlet and outlet connections. Another problem is that residual solvent recovery in the extraction unit is not possible.

A higher speed extraction process has been developed which involves boiling of the solvent while the sample is immersed in it. The solvent vapors are condensed on a cooling coil and drip back into the sample vessel. When the boiling phase of the process has been completed, the sample is lifted out of the solvent through manual operation of a cable system attached to the thimble that holds the sample. With the sample held above the level of the solvent, a washing phase of the process is carried out. During the washing phase, the solvent condensate drips onto the sample and back into the sample vessel. A solvent recovery phase is carried out by closing a manual shut-off valve which causes the solvent condensate to be collected in a collection chamber in the extraction unit. Following removal of the sample, the shut-off valve can be opened to drain the solvent from the collection chamber into a beaker.

Although this process is faster than the Soxhlet process, it is not altogether satisfactory, primarily because of the physical movements and the large number of manual operations that are required. During each cycle, the sample must be raised, the shut-off valve must be opened and closed, and the recovered solvent must be manually collected. Effective automation of fat extraction processes has proven to be technically difficult and unduly expensive, especially for continuous extraction units of the type used in laboratories.

The present invention has, as its principal goal, the provision of an improved fat extraction process which is carried out at automatically high speed. In accordance with the invention, four phases or steps are carried out in succession. First, the sample is boiled in solvent with simultaneous condensation and return of the condensate. Then, the solvent level is reduced until it is below the sample. Next, the sample is washed and wetted while remaining out of the solvent. Finally, the solvent is recovered in a collection vessel.

It is a particularly important feature of the invention that each phase of the extraction process is automatically initiated and terminated by a simple timer. The timer controls a valve which in turn causes an open topped funnel either to overflow or to drain the solvent condensate into an external collection vessel. Thus, all phases of the process are controlled automatically by the timer, and human intervention is required only during insertion and removal of the sample.

The invention is further directed to extraction apparatus on which the process can be carried out without mechanical movements or complicated parts. Because the drain valve determines whether or not the condensate will overflow from the funnel, the solvent level is wholly controlled by the valve and there is no need to raise or lower the sample or carry out other mechanical movements in the extraction unit.

By virtue of its nature, the apparatus of the present invention is well suited to process numerous samples simultaneously in different extraction units. The drain tubes of the different units should converge upstream from the control valve, thus draining the recovered solvent from each unit into a single collection vessel with only a single valve required for the plural extraction units. In this way, increased capacity can be provided for the processing of samples and a central collection system is provided for collecting all of the solvent that is recovered.

DESCRIPTION OF THE DRAWING

In the accompanying drawing which forms a part of the specification and is to be read in conjunction therewith and in which like reference numerals are used to indicate like parts in the various views:

FIG. 1 is a sectional view of an extraction unit that can be used to carry out a solvent extraction process according to the present invention, with the extraction unit depicted during the boiling phase of the process;

FIG. 2 is a diagrammatic elevational view similar to FIG. 1, but showing the extraction unit at the end of the solvent level lowering phase of the process;

FIG. 3 is a diagrammatic elevational view similar to FIGS. 1 and 2, but showing the extraction unit during the washing phase of the process; and FIG. 4 is a diagrammatic elevational view similar to FIGS. 1-3, but showing the extraction unit at the end of the solvent recovery phase of the process.

DETAILED DESCRIPTION OF THE INVENTION

Referring now to the drawing in more detail, and initially to FIG. 1, a fat extraction process in accordance with the present invention is preferably carried out by using an extraction unit which is generally identified by numeral 10. The extraction unit 10 includes a sample vessel 12 which seats on an explosion proof hot plate 14 or other type of heating device. A solid or semi-solid sample 16 from which fat is to be extracted is held in a thimble which is preferably constructed of screen wire or a similar material. Mounted on top of the sample vessel 12 by a flanged connection is a center section 20 of the extraction unit. A gasket 22 is fitted between mating flanges on the sample vessel 12 and center section 20. The thimble 18 is mounted within the sample vessel 12 by a spider 24 which permits the thimble to be quickly and easily inserted into and removed from the sample vessel. It is noted that the sample 16 is supported at a location well above the bottom of the sample vessel 12. The sample vessel 12 holds a quantity of a suitable solvent 26.

The solvent is condensed by a condensing unit 28 which is mounted on top of the center section 20 and which is equipped with a water cooled coil 30. Cooling water is pumped into the coil 30 through an inlet 32 and is discharged from the cooling coil through an outlet 34. The condensing unit 28 has a circular lower end 36 located within the center section 20 immediately above an open topped funnel 38. The funnel may be mounted in the center section 20 in any suitable manner. The funnel functions as an open topped container which catches condensate dripping from the cooling unit 28. The top rim of the funnel 38 is provided with a slot 40 through which the overflowing condensate discharges from the interior of the funnel, as will be explained more fully. The lower end of funnel 38 terminates in a small tip 42 which is centered directly above the thimble 18.

A drain tube 44 extends downwardly at an incline from a well located at the bottom of the interior of funnel 38. The drain tube 44 has its bottom or discharge end arranged to deliver condensate to an external collection vessel 46. The drain tube 44 is provided with a shut off valve 48 having open and closed positions. In the open position, liquid can freely drain through the drain tube 44 and into the collection vessel 46. In the closed position of valve 48, it blocks the flow of liquid into the collection vessel 46. The valve 48 is opened and closed by a suitable valve operator (not shown) controlled by a timer 50.

The sample vessel 12 is preferably provided with at least two graduation marks 52 and 54. The mark 52 is well above the level at which the sample 16 is held in the vessel 12. The other mark 54 is at a level well below that of the sample 16.

In carrying out the process of the present invention, the sample vessel 12 is filled with the solvent 26 up to the top graduation mark 52. The sample 16 is placed in thimble 18, and the thimble is then inserted into the sample vessel 12 such that the sample 16 is immersed in the solvent 26 at a location between the graduation marks 52 and 54. The hot plate 14 and the condensing unit 28 are then both activated, and the heating plate heats the solvent 26 to vaporization.

The initial phase of the process is a boiling phase in which the valve 48 is maintained closed by the timer 50. During the boiling phase, the solvent vapors rise through the center section 20 and are condensed on the cooling coil 30. The condensate then drips through the bottom end 36 of the condensing unit 28 into the open topped funnel 38. Since valve 48 is closed, the condensate does not drain into the collection vessel 46 but instead rises within the funnel. When the condensate fills the funnel 38, it begins to overflow through the discharge slot 40 and trickles down the outside surface of the funnel to the tip 42. The condensate drips from tip 42 in a series of drops, and is thus returned to the sample vessel 12 where it mixes with the rest of the solvent. The duration of the boiling phase of the process is controlled by the timer 50.

At the end of the boiling phase, the timer 50 opens valve 48 and thus initiates the second phase of the process in which the solvent level in the sample vessel 12 is lowered until it reaches the bottom graduation mark 54. During the level lowering phase, valve 48 remains open. Consequently, the solvent condensate which drips from the condensing unit into the funnel 38 is able to flow through the drain tube 44 and valve 48 into the collection vessel 46. The duration of the level lowering phase is controlled by the timer 50 and, when the solvent level in vessel 12 has dropped to approximately the lower graduation mark 54, the level lowering phase is terminated and valve 48 is closed by the timer 50. FIG. 2 depicts the solvent level in vessel 12 near the lower graduation mark 54 near the end of the level lowering phase of the process, and it is noted that a portion of the solvent has been directed into the external collection vessel 46.

The next or third phase of the process is a washing phase which is initiated when valve 48 is closed at the end of the level lowering phase. During the washing phase, the solvent condensate which is caught in the funnel 38 is not able to drain into vessel 46 because valve 48 remains closed. Consequently, the condensate eventually overflows funnel 38 and drips from the tip 42 onto the sample 16 which is centered below the tip. The condensate washes and wets the sample 16. During the washing phase, the vaporized solvent rises around the sample 16 and is then condensed and directed onto the sample in liquid form to wash and wet it.

The duration of the washing cycle is controlled by the timer 50 which opens valve 48 when the washing cycle has been completed. At the same time, the fourth and final phase of the process, namely, the solvent recovery phase, is initiated. During the solvent recovery phase, valve 48 is maintained open, and all of the solvent that is condensed in the condensing unit 28 and captured in the funnel 38 is drained into the collection vessel 46. When substantially all of the solvent has been removed from the sample vessel 12, the solvent recovery phase is completed. This completes the entire process, and the timer 50 then closes valve 48 and deenergizes the hot plate 14.

Several of the extraction units 10 can be operated at the same time to simultaneously process a number of different samples. In this situation, the drain tubes 44 of the different extraction units preferably join one another at a location upstream from the valve 48. Thus, the single valve 48 (controlled by the single timer 50) controls the process in a number of different extraction units, and the solvent which is recovered from the different units is collected in a single central collection vessel 46.

The fat extraction process of the present invention can be carried out in connection with the processing of various types of foods, including animal feeds. Various solvents can be used, including different types of ethers. It is noteworthy that the process progresses automatically under the programmed control of the timer 50, and human intervention is required only for the insertion of the sample at the start of the process and removal of the sample at the end of the process.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. A fat extraction process comprising the steps of:

immersing a sample containing fat in a solvent which is held in a sample vessel;

heating the solvent to effect vaporization thereof;

cooling the solvent vapors to effect condensation thereof;

returning the condensed solvent to the sample vessel during a boiling phase;

directing the condensed solvent to a collection vessel during a level lowering phase which follows the boiling phase and which is terminated when the solvent level in the sample vessel drops below the level of the sample;

directing the condensed solvent onto the sample during a washing phase which follows the level lowering phase; and directing the condensed solvent to the collection vessel during a solvent recovery phase which follows the washing phase and which is terminated when the sample vessel is substantially depleted of solvent.

2. The process of claim 1, wherein the step of directing the condensed solvent onto the sample comprises directing the solvent onto the sample in a series of drops.

3. The process of claim 1, wherein the step of returning the condensed solvent to the sample vessel comprises:
directing the condensed solvent into an open top container located above the sample; and
allowing the container to fill and overflow to return the solvent to the sample vessel under the influence of gravity.

4. The process of claim 3, wherein the step of directing the condensed solvent to the collection vessel during the level lowering phase comprises directing the solvent along a prescribed flow path from said container to the collection vessel at a sufficient rate to prevent the container from overflowing.

5. The process of claim 4, wherein the step of directing the condensed solvent to the collection vessel during the solvent recovery phase comprises directing the solvent along said prescribed flow path from said container to the collection vessel at a sufficient rate to prevent the container from overflowing.

6. The process of claim 4, wherein the step of directing the solvent along said prescribed flow path comprises:
providing a valve in the flow path for controlling the flow therethrough;
opening the valve to allow the solvent to begin flowing through the flow path at the start of the level lowering phase; and
closing the valve at the end of the level lowering phase to terminate flow through said flow path.

7. The process of claim 5, wherein the step of directing the condensed solvent to the collection vessel during the solvent recovery phase comprises opening the valve during the solvent recovery phase.

8. A solvent extraction process for extracting fat from a sample, said process comprising the steps of:
immersing the sample in solvent in a sample vessel;
effecting a boiling phase which comprises vaporizing the solvent followed by condensing the solvent vapors and returning the condensed solvent to the sample vessel;
effecting a level lowering phase which comprises vaporizing the solvent followed by condensing the solvent vapors and directing the condensed solvent to a collection vessel;
terminating the level lowering phase when the level of the solvent in the sample vessel is below the level of the sample;
effecting a washing phase which comprises vaporizing the solvent followed by condensing the solvent vapors and directing the condensed solvent onto the sample;
effecting a solvent recovery phase which comprises vaporizing the solvent followed by condensing the solvent vapors and directing the condensed solvent to the collection vessel;
terminating the solvent recovery phase when the sample vessel is substantially depleted of solvent; and
removing the sample from the sample vessel.

9. The process of claim 8, wherein the step of returning the condensed solvent to the sample vessel comprises:
catching the condensed solvent in an open top container located above the sample; and
allowing the container to fill with solvent and overflow such that the overflowing solvent falls back into the sample vessel.

10. The process of claim 9, wherein the step of directing the condensed solvent onto the sample comprises:
catching the condensed solvent in said container; and
allowing the container to fill with solvent and overflow such that the overflowing solvent falls onto the sample, 11. The process of claim 10, including the step of directing the overflowing solvent onto the sample in a series of successive drops.

12. The process of claim 9, wherein each step of directing the condensed solvent to the collection vessel comprises directing the solvent from said container along a prescribed flow path to the collection vessel at a flow rate sufficient to prevent overflow of the container.

13. The process of claim 12, wherein each step of directing the solvent along said prescribed flow path comprises opening the flow path during the level lowering and solvent recovery phases.

14. In a fat extraction process of the type in which a sample is immersed in solvent in a sample vessel and the solvent is heated to vaporization and thereafter condensed on a cooling device located above the sample, sample, wherein the improvement comprises the steps of:
intercepting the condensed solvent in a container interposed between the sample and the cooling device;
providing a flow path from the container to a collection vessel;
closing said flow path during a boiling phase to effect overflow of the container and return of the condensed solvent to the sample vessel;
opening said flow path during a level lowering phase to allow flow of condensed solvent along said flow path from the container to the collection vessel;
closing said flow path when the solvent level in the sample vessel is below the level of the sample;
maintaining said flow path closed during a washing phase to effect overflow of the container and application of the solvent to the sample; and opening said flow path during a level lowering phase t allow flow of condensed solvent along said flow path from the container to the collection vessel;

closing said flow path when the solvent level in the sample vessel is below the level of the sample;

maintaining said flow path closed during a washing phase to effect overflow of the container and application of the solvent to the sample; and opening said flow path during a solvent recovery phase to allow the solvent to flow from the container to the collection vessel until the sample vessel is substantially depleted of solvent.

15. The process of claim 14, wherein said washing phase is effected for a predetermined time period.

16. The process of claim 14, wherein the steps of opening and closing said flow path comprise respectively opening and closing a valve disposed to control flow through the flow path.

17. The process of claim 14, wherein said boiling phase is effected for a predetermined time period.

18. The process of claim 15, wherein said washing phase is effected for a predetermined time period.

19. Apparatus for use in a solvent extraction process in which fat is extracted from a sample, said apparatus comprising:

a sample vessel for holding solvent;

a sample holder in the sample vessel holding the sample at a preselected stationary location therein;

means for heating the solvent in the sample vessel to vaporization;

condensing means above the sample vessel for condensing the solvent vapors;

an open container situated between the sample vessel and condensing means at a location to receive solvent condensed by said condensing means, said container being arranged to direct solvent that overflows the container into the sample vessel during boiling and washing phases of the process;

a collection vessel;

a drain line extending from the container to the collection vessel to drain solvent to the collection vessel when the drain line is open; and a valve for opening and closing said drain line, whereby the valve can be closed during the boiling and washing phases and opened to drain solvent into the collection vessel during level lowering and solvent recovery phrases of the process.

20. Apparatus as set forth in claim 19, wherein said container presents a tip thereon effective to direct solvent that overflow the container toward the sample in a series of drops.

* * * * *